(12) United States Patent
Inagaki et al.

(10) Patent No.: US 9,384,956 B2
(45) Date of Patent: Jul. 5, 2016

(54) NEBULIZER AND ANALYSIS EQUIPMENT

(71) Applicants: NATIONAL INSTITUTE OF ADVANCED INDUSTRIAL SCIENCE AND TECHNOLOGY, Tokyo (JP); S.T.JAPAN INC., Tokyo (JP)

(72) Inventors: Kazumi Inagaki, Tsukuba (JP); Shin-Ichiro Fujii, Tsukuba (JP); Akiko Takatsu, Tsukuba (JP); Koichi Chiba, Tsukuba (JP); Takao Nakagawa, Tokyo (JP); Masaaki Abe, Tokyo (JP); Nobuyoshi Kitagawa, Tokyo (JP); Yosuke Nakagawa, Tokyo (JP)

(73) Assignees: National Institute of Advanced Industrial Science and Technology, Tokyo (JP); S.T. Japan Inc., Tokyo (JP)

( * ) Notice: Subject to any disclaimer, the term of this patent is extended or adjusted under 35 U.S.C. 154(b) by 0 days.

(21) Appl. No.: 14/367,944

(22) PCT Filed: Oct. 4, 2012

(86) PCT No.: PCT/JP2012/006370
§ 371 (c)(1),
(2) Date: Jun. 23, 2014

(87) PCT Pub. No.: WO2013/094093
PCT Pub. Date: Jun. 27, 2013

(65) Prior Publication Data
US 2014/0353495 A1    Dec. 4, 2014

(30) Foreign Application Priority Data
Dec. 22, 2011   (JP) .................. 2011-280713

(51) Int. Cl.
*H01J 49/10*   (2006.01)
*G01N 21/71*   (2006.01)
(Continued)

(52) U.S. Cl.
CPC ............. *H01J 49/105* (2013.01); *B05B 7/0416* (2013.01); *G01J 3/443* (2013.01); *G01N 21/714* (2013.01); *H01J 49/045* (2013.01)

(58) Field of Classification Search
USPC ......................................................... 250/288
See application file for complete search history.

(56) References Cited

U.S. PATENT DOCUMENTS

| | | | |
|---|---|---|---|
| 3,361,304 A | * | 1/1968 | Thompson ............ A61M 11/00 222/190 |
| 4,941,618 A | * | 7/1990 | Hildebrand ........... B05B 7/0416 128/200.14 |

(Continued)

FOREIGN PATENT DOCUMENTS

| JP | 9-166545 A | 6/1997 |
|---|---|---|
| JP | 2001-357815 A | 12/2001 |

(Continued)

OTHER PUBLICATIONS

Kazumi Inagaki, "Plasma Bunko Bunseki-yo Ko Kino Nebulizer no Kaihatsu Kokanshiki Dojiku Sanjukan Kozo no Shiryo Donyu Funmuki", AIST Today, Sep. 1, 2010, vol. 10, No. 9, p. 14.

(Continued)

Primary Examiner — Phillip A Johnston
(74) Attorney, Agent, or Firm — Sunstone IP

(57) ABSTRACT

A nebulizer characterized in being provided with: an inner tube, which is disposed coaxially with an outer tube in which a nebulizing outlet is formed and which, together with the outer tube, forms a gas channel therebetween; a sample channel, which is formed inside the inner tube and through which a liquid sample to be nebulized flows; and a reticular membrane disposed with a gap from the sample outlet that is formed at one end of the inner tube and in which multiple holes, through which liquid sample drops flowing out from the sample outlet pass along with a gas, are formed. Using the nebulizer, the particle size of the nebulized liquid droplets can be made uniformly fine over a broad range of sample liquid flow volumes while retention of sample liquid in the nebulizer is reduced.

5 Claims, 5 Drawing Sheets

(51) Int. Cl.
  *G01J 3/443*  (2006.01)
  *B05B 7/04*   (2006.01)
  *H01J 49/04*  (2006.01)

(56) References Cited

U.S. PATENT DOCUMENTS 5,435,282 A * 7/1995 Haber ............... A61M 15/0065
                                              128/200.14
5,732,885 A   3/1998 Huffman

FOREIGN PATENT DOCUMENTS

| JP | 2009-210435 A | 9/2009 |
| JP | 2011-59030 A  | 3/2011 |
| JP | 2011-59031 A  | 3/2011 |
| JP | 2011-196697 A | 10/2011 |

OTHER PUBLICATIONS

Kazumi Inagaki, Shin'ichiro Fujii, Akiko Takatsu, Koichi Chiba, Masaaki Abe, "ICP Hakko Bunseki-yo Ko Kino Nebulizer no Sekkei Kaihatsu", Abstracts of the Symposium of the Japan Society for Analytical Chemistry, May 1, 2010, vol. 71st, p. 114.

Kazumi Inagaki, Shin'ichiro Fujii, Akiko Takatsu, Koichi Chiba, Masaaki Abe, "Plasma Bunko Bunseki-yo Sankan Kozo Nebulizer no Funmu Tokusei Hyoka", Abstracts of the Symposium of the Japan Society for Analytical Chemistry, May 1, 2010, vol. 71st, p. 90.

International Search Report, PCT/JP2012/006370; International File Date: Oct. 4, 2012; 3 pgs.

* cited by examiner

| Sample Liquid Flow Rate | Experimental Example 1 | Comparative Example 1-1 | Comparative Example 1-2 |
|---|---|---|---|
| 0.010 mL/min | 2.27 μm | Nebulization can't be stabilized | 2.38 μm |
| 0.050 mL/min | 2.39 μm | Nebulization can't be stabilized | 2.65 μm |
| 0.100 mL/min | 2.42 μm | Nebulization can't be stabilized | 3.08 μm |
| 0.250 mL/min | 2.45 μm | 22.9 μm | 3.06 μm |
| 0.500 mL/min | 2.93 μm | 26.5 μm | 4.07 μm |
| 1.00 mL/min | 3.97 μm | 26.7 μm | 5.00 μm |

Fig.5

Droplet size distributions after nebulization by the nebulizers in Experimental Example 1 and Comparative Examples 1-1 and 1-2 (sample liquid flow rate: 0.5mL/min.)

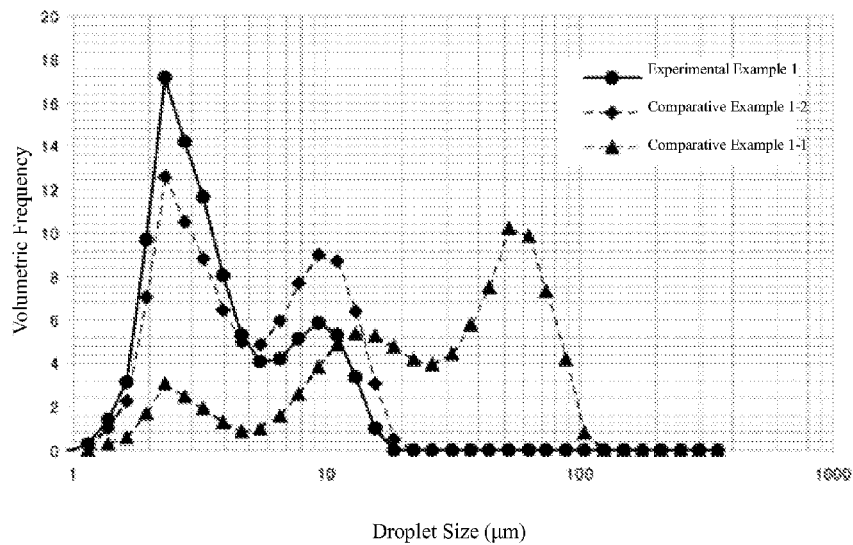

Fig.6

Atomic emission intensities of manganese in ICP-OES with the nebulizers in Experimental Example 2 and Comparative Examples 2-1 and 2-2

Sample Liquid Flow Rate (ml/min)

NEBULIZER AND ANALYSIS EQUIPMENT

CROSS-REFERENCE TO RELATED APPLICATIONS

This application claims priority to PCT Application No. PCT/JP2012/006370, having a filing date of Oct. 4, 2012, based off of JP Application No. 2011-280713, having a filing date of Dec. 22, 2011, the entire contents of which are hereby incorporated by reference.

FIELD OF TECHNOLOGY

The following relates to a nebulizer that sprays a test sample in aerosol state, i.e., a nebulizing mechanism, and an analysis equipment that employs the nebulizer.

BACKGROUND

Optical emission spectrometers or mass spectrometers that utilize plasma such as ICP (Inductively Coupled Plasma) as an atomization source or ionization source are widely used as general high-sensitivity element analysis equipment in the fields such as material analysis, environmental analysis, and trace analysis, etc.

In existing ICP-OES (ICP-Optical Emission Spectrometer), ICP-AES (ICP-Atomic Emission Spectrometer), or ICP-MS (ICP-Mass Spectrometer) equipment, to keep the plasma stable, the liquid sample become aerosol by means of a nebulizer (i.e., a nebulizing mechanism) in a vaporizing chamber, then, the aerosol sample is supplied to a plasma source and subjected to plasma treatment, and thus, analysis is made according to the optical emission from the plasma and the ionized sample.

In the nebulizer employed in such an analysis equipment, the following techniques are well known.

In patent document 1 (U.S. Pat. No. 4,941,618), there is a nebulizer with two parallel axes, namely with a flow channel (18) for a nebulizing gas to pass through and a flow channel (22) arranged in parallel to the flow channel (18) for a liquid to be nebulized to pass through, and the nebulizer comprises a first mesh screen (34) supported by a cap (36) downstream of the liquid flow channel (22), and a second mesh screen (38) arranged in front of the first mesh screen (34). The technique described in patent document 1 has the following structure: the first mesh screen (34) is wetted by the liquid in the flow channel (22), and then the liquid is blown by the high-speed gas from the parallel flow channel (18) to flow in droplets; in addition, the liquid droplets are refined by the second mesh screen (38) and then are nebulized.

In patent document 2 (JP2009-210435), the following triplex-tube concentric nebulizer is described, wherein, a hollow cylindrical outer tube, a hollow cylindrical intermediate tube, and a hollow cylindrical inner tube are arranged coaxially; the liquid sample or gas passes through the space formed inside the inner tube and the spaces formed between the tubes, so that the test sample is nebulized into fine liquid droplets efficiently.

SUMMARY

Technical Problem to be Solved by the Present Invention (Problems in the Prior Art)

In the nebulizer with two parallel axes described in patent document 1, the following structure is formed, wherein, the liquid that wets the first mesh screen with area much greater than the area of the gas outlet is squeezed by the gas into liquid droplets, and the liquid droplets are refined when they pass through the second mesh screen. Since the liquid droplets are only refined by the mesh screen without being shattered by the gas, large liquid droplets may be formed on the surface of the mesh screen owing to such as aggregating. Consequently, there may be deviation in the size of the liquid droplets. If there is deviation in the size of the liquid droplets, the amount of the liquid droplets and the quantity of the test sample contained in the liquid droplets may vary; in addition, the transport efficiency of droplets to the plasma may be decreased, or the intensity of the measured signal may not be stable.

Moreover, the nebulizer structure has the following problem: residual sample liquid may remain in the space among the meshes and in the meshes; consequently, the cleaning time required for changing the analyzed liquid to another liquid is longer than that of a concentric nebulizer. In addition, the previous flowing liquid may remain in the space among the meshes, resulting in contamination between the sample liquids. The lower the amount of the liquid flowing into the nebulizer is, the more serious the cleaning and contamination problems will be; therefore, this scheme is especially unsuitable for low-flow sample introduction structures where the loss of sample liquid must be controlled.

In the triplex-tube concentric nebulizer described in patent document 2, compared with the nebulizer with two parallel axes described in patent document 1, since there is little residual sample liquid, the nebulizer has shorter cleaning time, and can be used for a wide range of liquid flow. However, there is deviation in the size of nebulized liquid droplets. If there is deviation in the size of the liquid droplets, the amount of the liquid droplets and the quantity of the test sample contained in the liquid droplets may vary; in addition, the transport efficiency of the liquid droplets to the plasma may be decreased, or the intensity of the measured signal may not be stable.

In view of the above problems, the technical task of the present invention is to refine nebulized liquid droplets homogeneously directed to a wide range of sample liquid flow and reduce residual sample liquid in the nebulizer.

Technical Scheme

To solve the technical task described above, a nebulizer described in claim 1 comprises:

a cylindrical outer tube, with a nebulizing outlet formed at one end of the outer tube;

a cylindrical inner tube, arranged in the outer tube coaxially, with a gas flow channel formed between the inner tube and the outer tube for a nebulizing gas to pass through;

a sample flow channel, formed in the inner tube, for the liquid sample to be introduced to the nebulizing outlet for nebulization to pass through;

a mesh component, arranged at appropriate distance from a sample outlet formed at one end of the inner tube, with a plurality of holes for the liquid sample that flows out of the sample outlet and is to be nebulized by the nebulizing gas into liquid droplets to pass through along with the nebulizing gas.

The invention described in claim 2 relates to the nebulizer described in claim 1, and comprises the mesh component, which is woven with fibers, and has pores formed by the clearance among the fibers.

To solve the technical problems described above, an analysis equipment described in claim 3 comprises:

the nebulizer as described in claim 1 or 2;

a plasma source, which is supplied with nebulized sample in separated components nebulized by the nebulizer, and is designed to introduce the sample into plasma;
an analyzer, which analyzes the sample in plasma state.
Beneficial Effects:

Compared with concentric nebulizers that don't have a mesh component arranged at appropriate distance from the sample outlet, the inventions described in claims 1 and 3 can refine the size of nebulized liquid droplets homogeneously in a wide range of sample flow, and can reduce residual sample liquid in the nebulizer.

In the invention described in claim 2, the mesh component can be woven with fibers; thus, the problem of deviation in liquid droplet size can be settled with a low-cost structure.

BRIEF DESCRIPTION

Figure 7:
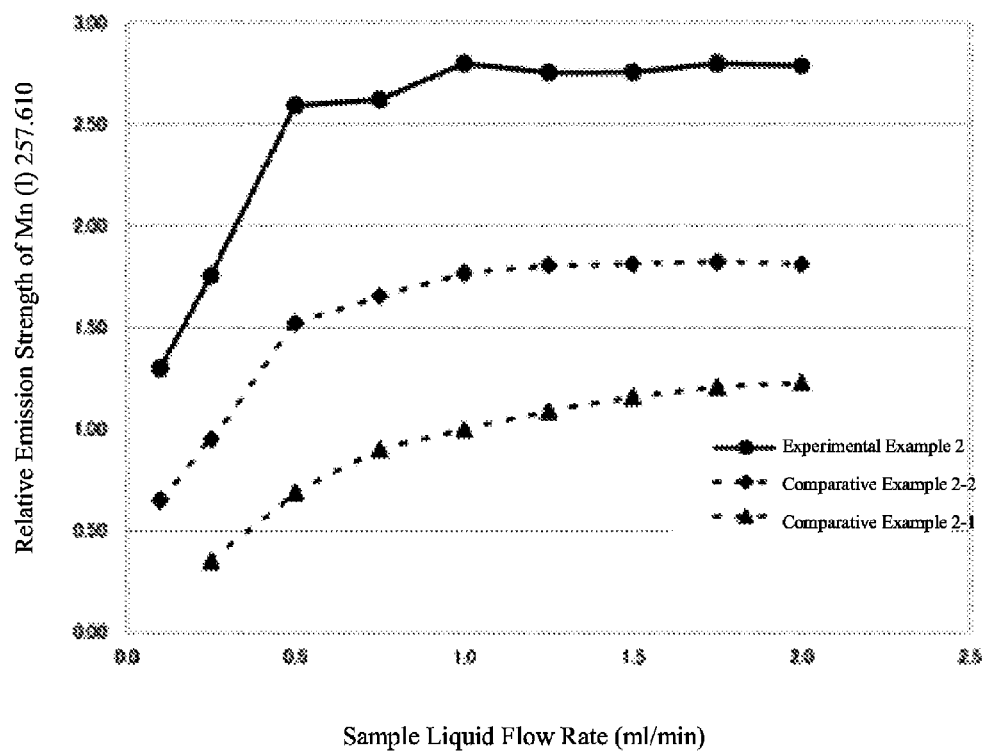

FIG. 5 shows a list of mean droplet sizes according to the experiment results of example 1, comparative example 1-1, and comparative example 1-2;

FIG. 6 shows the droplet size distributions according to the experiment results of example 1, comparative example 1-1, and comparative example 1-2, wherein the sample liquid flow rate is 0.5 mL/min, where, the horizontal axis represents liquid droplet size, and the vertical axis represents logarithm of volumetric frequency;

FIG. 7 shows the measured results of atomic emission intensities of manganese of example 2, comparative example 2-1, and comparative example 2-2, wherein, the horizontal axis represents flow rate of sample liquid, and the vertical axis represents relative emission intensity of manganese.

REFERENCE NUMBERS

1—analysis equipment;
3—nebulizer;
6—plasma source;
7, 8—analyzer;
11—outer tube;
11*a*—nebulizing outlet;
12—inner tube;
12*a*—sample outlet;
27—mesh component;
27*a*—fiber;
27*b*—pore;
R1—gas flow channel;
R2—sample flow channel

DETAILED DESCRIPTION

Hereunder some exemplary embodiments of the present invention will be described with reference to the accompanying drawings; however, the present invention is not limited to these embodiments.

Furthermore, in the following content that is described with reference to the accompanying drawings, the graphic representation of other components except for the components required for the description is omitted appropriately, for clarity purpose.

Example 1

Figure 1:
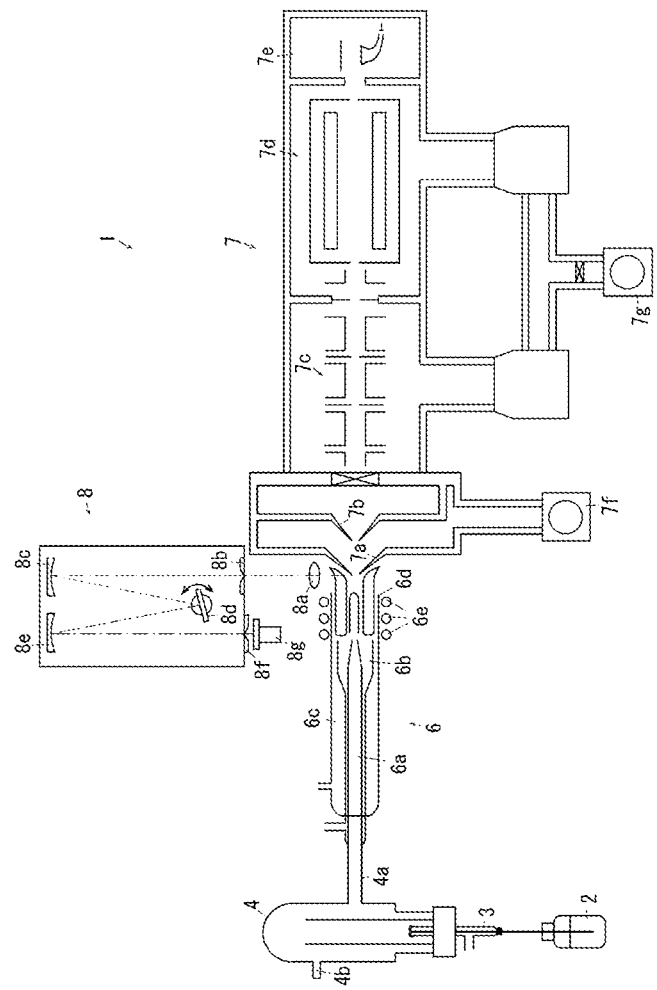
FIG. 1 is a schematic diagram of the analysis equipment in example 1.

FIG. 1 is a schematic diagram of the analysis equipment in example 1.

As shown in FIG. 1, the analysis equipment 1 in example 1 of the present invention has a sample container 2 that is designed to contain test sample. A liquid sample is contained in the sample container 2 in example 1. In addition, in this specification and the attached claims, a liquid sample refers to a test sample in liquid state, and also refers to liquid that contains a solid test sample dispersed, suspended, or dissolved therein. A nebulizer 3 that serves as a nebulizing mechanism is connected to the sample container 2. The nebulizer 3 will be described in detail in the following paragraphs. The front end of the nebulizer 3 is supported on a vaporizing chamber 4. In the vaporizing chamber 4, a plasma transport channel 4*a* for transporting the aerosol sample nebulized by the nebulizer 3 and a waste liquid discharge channel 4*b* are formed.

In the plasma transport channel 4*a*, as an example of a plasma source, a plasma torch 6 is connected. The plasma torch 6 has a triplex tube structure, and has a sample gas flow channel 6*a* connected with the plasma transport channel 4*a*, for aerosol sample to pass through; an auxiliary gas flow channel 6*b* arranged on the periphery of the sample gas flow channel 6*a*, for auxiliary gas (such as Ar gas) to pass through; and, a plasma gas flow channel 6*c* arranged on the periphery of the auxiliary gas flow channel 6*b*, for plasma gas to pass through. A coil 6*e* designed to generate inductive plasma is arranged at the front end 6*d* of the plasma torch 6 in such a way that it can supply high-frequency electric power for generating an electric field required for plasma treatment (for Ar etc.).

At the front end side of the plasma torch 6, as an example of analyzer, a mass spectrometer 7 is arranged. A test sample that is ionized by plasma is introduced into the mass spectrometer 7 through a conical sampling cone 7*a* and a skimmer cone 7*b*, converged by an ion lens 7*c*, and then is loaded into a mass analysis part 7*d* composed of a quadrupole mass filter. The ions sorted by the mass analysis part 7*d* are detected by an ion detector 7*e*. In the mass spectrometer 7 in example 1, a rotary pump 7*f* as an example of an exhaust unit between the sampling cone 7*a* and the skimmer cone 7*b*, or an ion lens 7*c*, or a turbo-molecular pump 7*g* as an example of an exhaust unit for exhaust from the mass analysis part 7*d*, is arranged.

In addition, the mass spectrometer 7 in example 1 can be a Q-MS (Quadrupole-Mass Spectrometer), but is not limited to Q-MS, which is to say, any mass spectrometer known in the prior art can be used.

Moreover, at a side of the front end of the plasma torch 6, as an example of an analyzer, an optical emission spectrometer 8 is arranged. The optical emission spectrometer 8 in example 1 comprises a focusing system 8*a*, which focuses the emitted light; an entry slit 8*b*, which slits the light focused by the focusing system 8*a*; a concave lens 8*c*, which reflects the light that passes through the entry slit 8*b*; a diffraction grating 8*d*, which carries out light splitting for the light reflected by the concave lens 8*c*; a concave lens 8*e*, which reflects the light split through the diffraction grating 8*d*; an exit slit 8*f*, which slits the light reflected by the concave lens 8*e*; a detector 8*g*, which detects the light that passes through the exit slit 8*f*.

In addition, the optical emission spectrometer 8 in example 1 is not limited to the structure described above, which is to say, any known optical emission spectrometer in the prior art can be used.

(Description of the Nebulizer)

Figure 2:
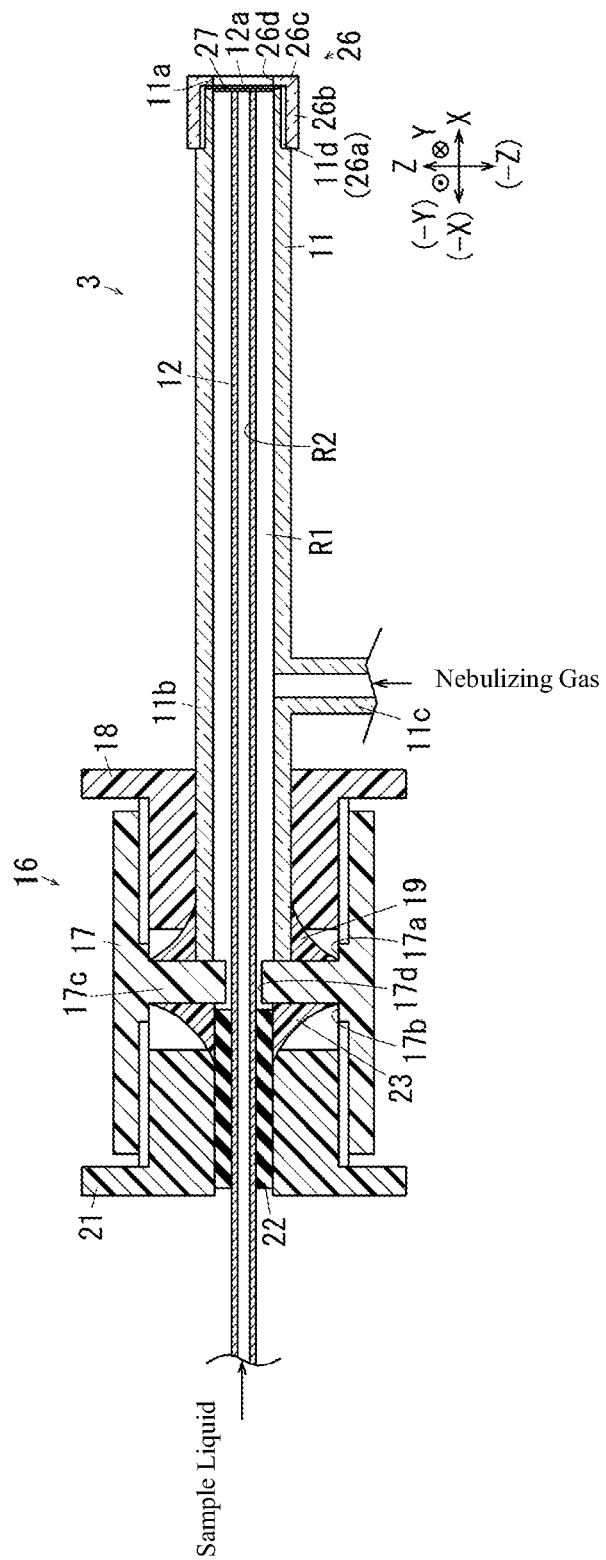
FIG. 2 is a schematic diagram of the overall structure of the nebulizer in example 1.

FIG. 2 is a schematic diagram of the overall structure of the nebulizer in example 1.

Figure 3:
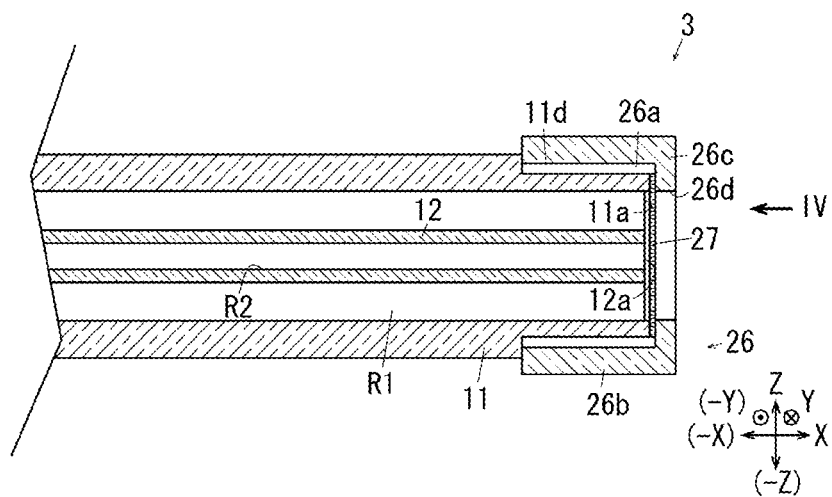
FIG. 3 is an enlarged view of the front end part of the nebulizer in example 1.
Figure 4:
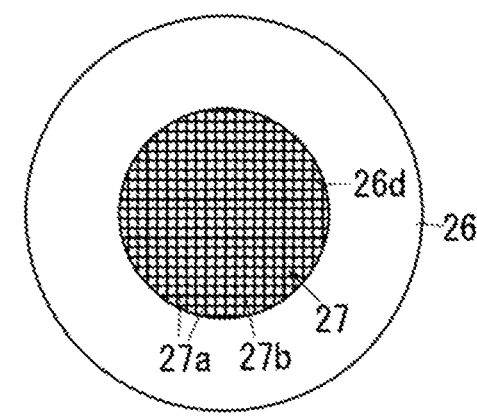
FIG. 4 is a schematic diagram of the main part of the mesh component in example 1, when viewed in a direction indicated by the arrow IV in FIG. 3.

FIG. 3 is an enlarged view of the front end part of the nebulizer in example 1.

In addition, for better understanding of the following content, in the accompanying drawings, the front-back direction is defined as X direction, the left-right direction is defined as Y direction, and the up-down direction is defined as Z direction; the arrow X, –X, Y, –Y, Z, or –Z means front, back, right, left, up, or down direction/side respectively.

Moreover, in the drawings, a symbol "◯" with a "•" in it refers to an arrow from the inner side of the paper towards the outer side of the paper, while a symbol "◯" with a "x" in it refers to an arrow from the outer side of the paper towards the inner side of the paper.

As shown in FIG. 2, the nebulizer 3 in example 1 has a hollow cylindrical outer tube 11. As shown in FIG. 2 and FIG. 3, at the front end of the outer tube 11, a nebulizing outlet 11a is formed; in the base end 11b, a fluid introduction part 11c that can be used to introduce the nebulizing gas, as an example of fluid, is formed. In addition, on the outer surface of the front end of the outer tube 11, a thread part 11d, as an example of a fastening part, is formed.

In FIG. 2 and FIG. 3, as an example of the hollow cylindrical inner tube, a capillary tube 12 is arranged in the outer tube 11 coaxially. As an example of a fluid flow channel, a gas flow channel R1 for the nebulizing gas to pass through is formed between the capillary tube 12 and the outer tube 11; a sample flow channel R2 is formed in the capillary tube 12. In the capillary tube 12 in example 1, the front sample outlet 12a is arranged near the nebulizing outlet 11a, and the left end runs through the outer tube 11 and extends leftwards, and is supported on a fixing tube joint 16 as an example of an inner tube fixing part.

The fixing tube joint 16 has a cylindrical tube joint body 17. In the tube joint body 17, a pair of recessed parts 17a and 17b that extend from the two ends in axial direction is formed, and a partition wall 17c is formed between the recessed parts 17a and 17b. A thread groove is formed on the inner peripheral surface of each of the recessed parts 17a and 17b, and an opening 17d that connects the recessed parts 17a and 17b is formed in the partition wall 17c. The right recessed part 17a receives the left end of the outer tube 11, i.e., base end 11b of the outer tube 11. The left end of the outer tube 11 is supported in such a way that a first fixing screw 18 that is engaged with the thread groove on the inner peripheral surface of the recessed part 17a penetrates the left end; on the left end of the outer tube 11, a first cap 19, as an example of a sealing element that seals the space between the outer tube 11 and the partition wall 17c, is mounted.

In addition, in the left recessed part 17b, a second fixing screw 21 that is engaged with the thread groove on the inner peripheral surface is mounted; on the second fixing screw 21, the capillary tube 12 is supported via a Teflon sleeve 22 in communicating state, as an example of a low-friction material that belongs to an elastic material. On the inner end of the sleeve 22, a second cap 23 is mounted, as an example of a sealing element. In addition, in the fixing tube joint 16 in example 1, the tube joint body 17, fixing screws 18 and 21, and caps 19 and 23 are made of resin material. Preferably, a sleeve 22 is also provided; but it can be omitted as required.

Therefore, the capillary tube 12 in example 1 can be fixed to the outer tube 11 via the fixing tube joint 16 by tightening up the second fixing screw 21, and can be removed from the outer tube 11 by unscrewing the second fixing screw 21. Thus, the capillary tube 12 in example 1 is supported on the outer tube 11 in a removable manner. Moreover, in example 1, the position of the capillary tube 12 can be adjusted by means of the fixing tube joint 16; thus, the position of the sample outlet 12a can be adjusted accurately.

The hollow cylindrical capillary tube 12 is connected with the sample container 2, and the sample R2 can flow in the sample flow channel R2 in the capillary tube 12.

In FIG. 3, in the nebulizer 3 in example 1, a mesh retainer 26, as an example of a mesh component retaining body, is supported on the front end of the outer tube 11. The mesh retainer 26 in example 1 has a hollow cylindrical tube part 26b and a plate-shaped retaining part 26c, a thread part 26a for the thread part 11d to be screwed into is formed on the inner peripheral surface of the tube part 26b, and the retaining part 26c is arranged on the front end of the tube part 26b. In the retaining part 26c, an opening 26d is formed in front of the nebulizing outlet 11a.

On the inner side of the retaining part 26c, a mesh sheet 27, as an example of the mesh component, is supported. The mesh sheet 27 in example 1 is arranged in front of the nebulizing outlet 11*a*, with its peripheral part being supported on the retaining part 26*c*. Thus, with the mesh sheet 27 being supported on the inner side of the mesh retainer 26, the thread part 26*a* of the mesh retainer 26 is secured to the thread part 11*d* of the outer tube 11, so that the mesh sheet 27 is retained in front of the nebulizing outlet 11*a* at appropriate distance. In addition, in example 1, the distance between the mesh sheet 27 and the nebulizing outlet 11*a* is set to 100 μm, but it is not limited to that value, which is to say, the distance can be set freely; preferably, it is within a range of 25~200 μm.

FIG. 4 is a schematic diagram of the main part of the mesh component in example 1, when viewed in a direction indicated by the arrow IV in FIG. 3.

In FIG. 4, the mesh sheet 27 in example 1 is a sheet woven with nylon fibers 27*a*, as an example of resin material, with pores 27*b* formed among the fibers. If the size d1 of the pores 27*b* is too small, the pores 27*b* may be jammed by the liquid; whereas, if the size d1 is too great, the diameter of the aerosol liquid droplets will be too large. Therefore, in example 1, d1 is set to 15 μm, preferably within the range of 5~20 μm.

Effects of Example 1

In the nebulizer 3 with the structure described above in example 1, if argon gas (Ar), as an example of nebulizing gas, is introduced through the fluid introduction part 11*c*, in relation to the front end of the capillary tube 12, the liquid sample is in aerosol state and is injected through the nebulizing outlet 11*a* into the vaporizing chamber 4, and then is ionized by the plasma torch 6; next, the sample in plasma state is measured and analyzed by the mass spectrometer 7 or optical emission spectrometer 8.

In the concentric nebulizer 3 that can refine liquid droplets in example 1, compared with nebulizers with two parallel axes, when the liquid droplets of sample nebulized by the nebulizing outlet 11*a* pass through the mesh sheet 27, they will be further refined, and have uniform size; thus, the mean size of the liquid droplets can be decreased.

In addition, in the specification of present application, the mean droplet size refers to droplet size with 50% volume integral value of size distribution calculated with a laser diffraction-scattering method.

EXPERIMENTAL EXAMPLES

Hereunder some experiments for proving the functions of the nebulizer in example 1 will be described.

Experimental Example 1

In experimental example 1, pure water is used as the liquid sample, argon (Ar) gas is used as the nebulizing gas, and at a distance of 5 mm from the mesh sheet, the size distribution of the sample liquid droplets after the liquid droplets pass through the mesh sheet is measured with a laser diffraction-scattering method.

In addition, in experimental example 1, the size distribution values are measured under the conditions that sample liquid flow rate equals to 0.010 mL/min, 0.050 mL/min, 0.100 mL/min, 0.250 mL/min, 0.500 mL/min, and 1.000 mL/min, nebulizing gas flow rate equals to 1 L/min, and pores 27*b* of mesh sheet 27 equals to 15 μm respectively, and the mean droplet size is calculated.

Comparative Example 1-1

In comparative example 1-1, a conventional concentric nebulizer available in the market is used, and the size distribution value is measured, and the mean droplet size is calculated in the same way as that in experimental example 1, at a distance of 5 mm from the front end of the nebulizing nozzle.

Comparative Example 1-2

In comparative example 1-2, a triplex tube concentric nebulizer described in patent document 2 is used, and the size distribution value is measured, and the mean droplet size is calculated in the same way as that in experimental example 1, at a distance of 5 mm from the front end of the nebulizing nozzle.

The experimental results are shown in FIG. 5 and FIG. 6.

FIG. 5 shows a list of mean droplet sizes according to the experiment results of example 1, comparative example 1-1, and comparative example 1-2.

In FIG. 5, according to the experimental results, in the nebulizer in experimental example 1, the mean droplet size is within a range of 2.27~3.97 μm, and increases as the flow rate of the test liquid increases; in contrast, in the conventional concentric nebulizer in comparative example 1-1, the mean droplet size is within a range of 22.9~26.7 μm, which is very large; in the triplex tube concentric nebulizer in comparative example 1-2, the mean droplet size is within a range of 2.38~5.00 μm, and increases as the flow rate of the test liquid increases; compared with the mean droplet size in experimental example 1, the flow rate of any sample is higher.

Especially, it is proved in comparative example 1-1 that at a flow rate of 0.100 ml/min or lower, it is unable to nebulize stably, and it is difficult to introduce the sample.

FIG. 6 shows the droplet size distributions according to the experiment results of example 1, comparative example 1-1, and comparative example 1-2, wherein the sample liquid flow rate is 0.5 mL/min, where, the horizontal axis represents liquid droplet size, and the vertical axis represents logarithm of volumetric frequency.

In FIG. 6, according to the graph of liquid droplet size vs. volumetric frequency (observed frequency on the basis of the volumes of liquid droplets in different sizes), in the comparative example 1-1, the frequency of 50 μm liquid droplets is the highest; in that case, it is proved that the refinement is inadequate. In the comparative example 1-2 and the experimental example 1, the frequency of 2.2 μm liquid droplet is the highest; however, compared with the comparative example 1-2, it is proved that the frequency of 2.2 μm liquid droplets is the highest and the proportion of refined liquid droplet is higher in experimental example 1.

Thus, it can be seen from FIG. 5 and FIG. 6 that compared with comparative example 1-2, in experimental example 1, the mean droplet diameter is further decreased, the proportion of refined liquid droplets is higher, the deviation in droplet size is lower, and fine liquid droplets can be supplied stably. Therefore, it is easier to introduce the test sample stably at a lower flow rate.

In addition, in FIG. 6, in the experimental results in experimental example 1 and comparative example 1-2, the frequency of 9 μm liquid droplets is high because the nebulized liquid droplets contact with each other (aggregation) and form a bigger liquid droplet; moreover, in the case of experimental example 1, it is believed that the mesh sheet 27 inhibits aggregating of the liquid droplets; therefore, the frequency is lower when compared with the value in comparative example 1-2.

Experimental Example 2

In experimental example 2, the atomic emission intensity of manganese is measured at 257.610 nm wavelength under the following conditions: the nebulizer in experimental example 1 is mounted in ICP-OES, and the standard liquid of manganese with a concentration of 1 mg/L is introduced as the sample liquid.

In experimental example 2, the atomic emission intensities of manganese are measured under the conditions of sample liquid flow rate=0.10 mL/min, 0.25 mL/min, 0.50 mL/min, 0.75 mL/min, 1.00 mL/min, 1.25 mL/min, 1.50 mL/min, 1.75/mL/min, and 2.00 mL/min, nebulizing gas flow rate=0.5 L/min, and pores 27*b* of mesh sheet 27=15 μm.

Comparative Example 2-1

In comparative example 2-1, the atomic emission intensity of manganese is measured with the same conventional concentric nebulizer in comparative example 1-1 in the same way as that in experimental example 2.

Comparative Example 2-2

In comparative example 2-2, the atomic emission intensity of manganese is measured with the same triplex tube concentric nebulizer in comparative example 1-2, which is described in patent document 2, in the same way as that in experimental example 2.

The experimental results are shown in FIG. 7.

FIG. 7 shows the measured results of atomic emission intensities of manganese in example 2, comparative example 2-1, and comparative example 2-2, wherein, the horizontal axis represents flow rate of sample liquid, and the vertical axis represents relative emission intensity of manganese.

In FIG. 7, according to the experimental results, the emission intensity of manganese in the nebulizer in experimental example 2 is 2.2 times of that in the conventional concentric nebulizer in comparative example 2-1 or higher, and is 1.5 times of that in the triplex concentric tube nebulizer described in patent document 2 in comparative example 2-2 or higher. Thus, it is proved that the intensity of the signal observed in the observation unit is higher, and observation at a higher sensitivity is possible in the nebulizer in example 1, when compared with the structures in the prior art.

Therefore, in the nebulizer 3 in example 1, the nebulized liquid droplets can be refined more easily through mesh sheet 27 and the droplet size is more uniform; thus, stable and efficient nebulization is possible. As a result, the efficiency of liquid droplet transport to the plasma unit can be improved, and the intensity of the signal measured with the mass spectrometer 7 or optical emission spectrometer 8 is high.

Hence, unlike the electrospray ion technique that applies high voltage and sprays charged samples, the nebulizer 3 in example 1 doesn't require application of high voltage or any special tubing technique, and can be applied easily in existing ICP-OES/MS apparatuses. In addition, the nebulizer 3 in example 1 is a concentric nebulizer in which the capillary tube 12 and the outer tube 11 are arranged coaxially. In the nebulizer 3, the processing is easier, the liquid droplets can be refined more easily, the nebulization efficiency is higher, and stable nebulization is possible, when compared with the 2-axis parallel nebulizer described in patent document 1 and known nebulizers in which the sample flow channel and gas flow channel are arranged perpendicularly at 90° in relation to each other (i.e., in a cross flow form) in the prior art.

Moreover, in the nebulizer 3 in example 1, the capillary tube 12 is mounted in a removable manner; thus, the capillary tube 12 can be adjusted (tuned) in relation to the position of the outer tube 11 or nebulizing outlet 11a, when compared with structures in which the capillary tube is mounted in a non-removable manner. Thus, deviations in nebulization efficiency resulted from manufacturing error and the like can be inhibited.

Furthermore, the capillary tube 12 or outer tube 11 can be replaced easily; thus, a worn or contaminated capillary tube 12 can be replaced and cleaned easily. In addition, compared to the case that appropriate nebulizers have to be prepared for different test samples according to the properties of the test samples, in example 1, multiple capillary tubes 12 can be prepared for different test samples, so that the test samples can be handled with one outer tube 11 simply by replacing the capillary tube.

In addition, in the nebulizer 3 in example 1, the mesh retainer 26 is supported in a removable manner by thread tightening, which is to say, the used mesh sheet 27 can be replaced easily by removing the mesh retainer 26. Thus, in case the performance of the mesh sheet 27 is degraded, it can be replaced easily to introduce another test sample. As a result, the detrimental effect of residues in the previous test to the present test can be reduced.

Moreover, in example 1, the mesh sheet 27 is woven with fibers; therefore, such mesh sheets can be produced by mass production with known technology, and mesh components can be manufactured with a low-cost structure.

(Variants)

Though the present invention is described with above examples, the present invention is not limited thereto. A variety of variations can be made within the essential scope of the present invention as defined in the claims. Hereunder some variants of the present invention (H01)~(H08) will be described.

(H01) The values and materials are not limited to those values and materials listed in the above examples, which is to say, they can be altered appropriately according to the design, form, and purpose, etc.

(H02) Though exemplary analysis equipments 1, including mass spectrometer 7 and optical emission spectrometer 8, are described in above examples, the analysis equipment is not limited to those structures. For example, the analysis equipment can comprise either of the structures, or comprises an analyzer that is different from the analyzers described above.

(H03) In above examples, preferably the capillary tube 12 has a removable structure; however, it can be formed into an integral structure, if it is impractical to design or manufacture the capillary tube in a removable structure.

(H04) In above examples, the liquid sample can be separated foe each component alternatively, i.e., for the analysis, a column (separating column) for chromatography can be connected between the nebulizer 3 and the sample container 2, and the test sample can be nebulized in separated state. Alternatively, instead of using a column, an integral organic piece can be formed in the capillary tube 12, or a filling material such as the silicone described in the document JP2003-151486 or JP2005-134168 can be filled, or a rod-shaped porous piece with pores in different sizes can be used, so that the components are separated in the capillary tube 12 and then nebulized. For an integral organic piece, for example, per 1 ml solution, 150 μL glycidyl methacrylate, 50 μL ethylene glycol dimethacrylate, 467 μL normal propyl alcohol, 266 μL 1,4-butylene glycol, 67 μL water, and 2 mg 2,2'-azodiisobutyronitrile are filled into the capillary tube 12 and sealed in the capillary tube 12; then, the solution is heated up to 60° C. and held for 24 h for thermal polymerization; next, the pore forming agent is removed with methyl alcohol, so as to form an integral organic piece with a porous structure. The separating media (integral organic piece and filling agent) are loaded in the capillary tube 12 and directly nebulized from the capillary tube 12. The components are separated by means of a separating column and through the tubing, dispersion of separated components can be reduced compared with separated structure, i.e., the dead volume can be zero. In addition, preferably the separating media are formed in the front end of the capillary tube 12; alternatively, the separating media can be formed near the front end, or formed in part of the capillary tube 12 instead of the entire capillary tube 12.

(H05) According to above examples, when analysis is made for a test sample that contains hexavalent chrome or trivalent chrome, As, or Se, etc., which has charges, anion exchange based chemical modification, Cr adsorption, or component separation can be carried out for the test sample in the capillary tube 12. Moreover, structures formed integrally with the variant (H03) can be combined on the capillary tube 12. Likewise, in case the sample contains components that have negative charges, cation exchange based chemical modification can be carried out. Especially, the capillary tube 12 in the example 1 or 2 can be formed in a removable manner; a capillary tube in which anion exchange based chemical modification is carried out can be prepared, and a capillary tube in which cation exchange based chemical modification is carried out can be prepared; thus, to analyze different samples, the capillary tube can be replaced simply, while the outer tube 11 can be shared among the test samples.

(H06) According to above examples, a concentric structure is described; however, it is not limited thereto; for example, a triplex tube structure, quadruplex tube structure, or quintuplex tube structure can be formed.

(H07) According to above examples, as for the mesh component, a mesh sheet 27 woven with nylon fibers is described; however, the mesh component is not limited to that, which is to say, an appropriate mesh component can be used according to the properties of the test sample. Alternatively, for example, a porous membrane made of resin (e.g., polyimide resin) or porous metal (e.g., Pt) can be used, or a silicon mesh screen formed by photolitho etching in a silicon wafer can be used, or a porous fluoro resin mesh screen formed by laser ablation in fluoro resin (e.g., PTFE or PFA) can be used. In addition, in case that the test sample contains fluorhydric acid that may dissolve glass, when a fluoro resin mesh screen is to be used, preferably a fluoro resin coating that is resistant to hydrofluoric acid is applied on the inner side of the outer tube 11.

(H08) According to above examples, the following structure can be formed, i.e., a pump is arranged when liquid sample is introduced. In addition, an eluent can be introduced by the liquid flow pump, and a syringe can be arranged in the flow-line to inject the test sample into the eluent.

The invention claimed is:

1. A nebulizer, comprising:
    a cylindrical outer tube, with a nebulizing outlet formed at one end of the outer tube;
    a cylindrical inner tube arranged in the outer tube and aligned coaxially therewith, to form a gas flow channel and a sample flow channel, the gas flow channel defined between the inner and outer tubes and the sample flow channel defined by the inner tube; and
    a mesh component, arranged and supported at the nebulizing outlet, with a plurality of holes for a liquid sample that flows out of the sample flow channel and is to be nebulized by a nebulizing gas into liquid droplets to pass through along with the nebulizing gas.

2. The nebulizer according to claim 1, comprising the mesh component, which is woven with fibers, and has pores formed by the clearance among the fibers.

3. The analysis equipment, comprising:
    the nebulizer as described in claim 1;
    a plasma source, which is supplied with nebulized sample in separated components nebulized by the nebulizer, and is designed to introduce the sample into plasma; and
    an analyzer, which analyzes the sample in plasma state.

4. The nebulizer according to claim 1, wherein a cross section of the gas flow channel is a ring-shape extending in an axial direction.

5. The nebulizer according to claim 1, wherein the liquid sample is introduced to the nebulizing outlet at the sample outlet.

* * * * *